(12) United States Patent
Tao

(10) Patent No.: US 8,907,100 B2
(45) Date of Patent: Dec. 9, 2014

(54) LANSOPRAZOLE COMPOUND AND NOVEL PREPARATION METHOD THEREOF

(75) Inventor: Linggang Tao, Wuyi (CN)

(73) Assignee: Hainan Lingkang Pharmaceutical Co., Ltd., Hainan (CN)

( * ) Notice: Subject to any disclaimer, the term of this patent is extended or adjusted under 35 U.S.C. 154(b) by 0 days.

(21) Appl. No.: 14/119,370

(22) PCT Filed: Dec. 27, 2011

(86) PCT No.: PCT/CN2011/002201
§ 371 (c)(1),
(2), (4) Date: Nov. 22, 2013

(87) PCT Pub. No.: WO2013/078578
PCT Pub. Date: Jun. 6, 2013

(65) Prior Publication Data
US 2014/0275550 A1   Sep. 18, 2014

(30) Foreign Application Priority Data
Nov. 28, 2011 (CN) .......................... 2011 1 0384748

(51) Int. Cl.
*C07D 401/12* (2006.01)

(52) U.S. Cl.
CPC .................................... *C07D 401/12* (2013.01)
USPC ....................................................... 546/273.7

(58) Field of Classification Search
USPC ........................................................ 546/273.7
See application file for complete search history.

(56) References Cited

PUBLICATIONS

Zhang, "Method for preparing, etc.," CA 151:389244 (2009).*

* cited by examiner

*Primary Examiner* — Patricia L Morris
(74) *Attorney, Agent, or Firm* — CBM Patent Consulting, LLC

(57) ABSTRACT

A process for purifying lansoprazole comprises 1) loading crude lansoprazole material onto a macroporous resin column; 2) concentrating the eluate from the column in a crystallization vessel by vacuum; 3) seeding lansoprazole crystal; 4) crystallizing the lansoprazole; 5) separating the precipitated crystals. The process especially has large processing capacity, can be carried out continuously and therefore suitable for industrial production, improving the quality of formulated products and reducing side effects.

9 Claims, No Drawings

LANSOPRAZOLE COMPOUND AND NOVEL PREPARATION METHOD THEREOF

This application is the U.S. national phase of International Application No. PCT/CN2011/002201 Filed 27 Dec. 2011 which designated the U.S. and claims priority to Chinese Application No. 201110384748.2 filed 28 Nov. 2011, the entire contents of each of which are hereby incorporated by reference.

1. Field of the Invention

The present invention relates to a highly pure lansoprazole compound and its preparation method, and belongs to the medical technical filed.

2. Background Art

Lansoprazole, chemical name 2-[[[3-methyl-4-(2,2,2-trifluoroethoxy)-2-pyridinyl]methyl]sulfinyl]-1H-benzimidazole, CAS number: 103577-45-3, has the molecular formula of $C_{16}H_{14}F_3N_3O_2S$ and the molecular weight of 369.36. The structure of lansoprazole is as follows:

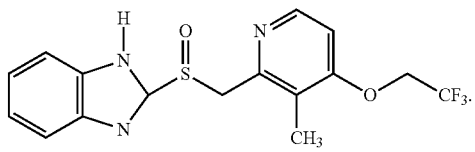 [SMILES: Cc1c(OCC(F)(F)F)ccnc1CS(=O)C1Nc2ccccc2N1]

Lansoprazole is a well-known gastric proton pump inhibitor, which can inhibit gastric acid secretion and is used as an antiulcer agent.

A number of references of patents have disclosed processes for synthesizing lansoprazole. Several methods involve the use of lansoprazole precursor with a thioether group, in which the thioether group is oxidized.

EP 0174726B1 discloses the use of a peracid, such as m-chloroperbenzoic acid, sodium bromite, sodium hypochlorite or hydrogen peroxide as the oxidizing agent. Oxidation is carried out in a halogenated hydrocarbon, an amide, an alcohol or a mixture thereof.

EP 0302720A1 discloses an approach of using hydrogen peroxide in the presence of a vanadium compound such as vanadium pentoxide, sodium metavanadate or vanadium acetylacetonate to prepare lansoprazole.

According to WO 02/062786A1, tert-butyl hydroperoxide (TBHP) is used in the presence of vanadium pentoxide, sodium metavanadate or vanadium acetylacetonate to prepare lansoprazole. Oxidation is preferably carried out in toluene or isopropanol.

WO 2004/011455A1 discloses a method of using tert-butyl hydroperoxide (TBHP) in the presence of vanadium oxychloride to prepare lansoprazole, wherein the reaction is carried out in a solvent such as C1-C5 alcohols, decane, nonane, toluene or a mixture thereof with water.

Vanadium oxychloride is used in the presence of an alcohol. Further, the reaction is preferably carried out in the presence of a weak base. Crude lansoprazole can be obtained with up to 90% yield.

WO 03/008406A1 relates to the preparation method of the benzimidazole compound, by reacting the corresponding precursor with an oxidizing agent in a suitable solvent, followed by extraction of sulfone byproducts and isolation of the product. Preferably m-chloroperbenzoic acid is used as the oxidizing agent.

Currently, lansoprazole is manufactured mainly in accordance with the prior art methods or dependent on dispensing from imported raw material drugs by domestic pharmaceutical manufacturers. However, these products have relatively low purity, especially when using conventional crystallization methods for purification, wherein crystallization yield is low, crystallization cycle is lengthy, crystals have poor polymorph, poor uniformity and poor mobility and cannot meet the requirements for pharmaceutical needs. Therefore, how to improve the purity of lansoprazole is a pending problem anxiously to be solved, which possesses significant social and economic benefits.

DETAILED DESCRIPTION OF THE INVENTION

The present invention discloses a process for purification of lansoprazole compound. The lansoprazole used in the refining process provided in the present invention is lansoprazole crude materials prepared by known synthetic methods or lansoprazole raw materials obtained commercially or by import.

The inventors found after intensive studies that the purity of lansoprazole crude materials can be greatly improved by the purification method which comprises the following steps:

first, crude lansoprazole is isolated and purified using a macroporous resin column, eluted with an eluent and the eluate is collected;

then, the eluate is subjected to vacuum crystallization, comprising the steps of:

step 1), at least half or more of the eluate containing lansoprazole is added into a crystallization vessel and concentrated first under negative pressure and elevated temperature;

step 2), then the temperature is lowered and lansoprazole crystal seeds are added;

step 3), when fine crystal grains appear, maintaining the materials in the crystallization vessel at a boiling and concentrated state, the remaining eluate containing lansoprazole is added into the crystallization vessel, crystallization continues by keeping the temperature, and optionally the temperature may be adjusted or lowered, so that the lansoprazole solution in the crystallization vessel can further grow crystals;

step 4), the precipitated crystals are separated, washed and dried to provide refined lansoprazole.

The following is detailed description of the invention.

According to the present invention, first, crude lansoprazole is isolated and purified using a macroporous resin column, eluted with an eluent and the eluate is collected.

Macroporous adsorption resins are a class of cross-linked polymer with better adsorption properties developed in the past ten years. They have many advantages such as good macroporous mesh structure, large surface area, excellent physical and chemical stability, easy regeneration, energy efficiency etc. They can be widely used in the separation and purification of active ingredients and has great application values in the environmental area, food and medicine and other areas. Adsorption resins are mainly classified as non-polar, weakly polar and polar resins according to different polarity. Currently the most commonly used resins are of styrene type and acrylonitrile type. Adsorption properties of adsorption resins are the results of van der Waals force or hydrogen bonding, while the network structure and large surface area contribute to their filter and separation capabilities. Macroporous adsorption resins are separation materials with the combination of adsorption and separation theories.

Lansoprazole crude material may be loaded directly to an adsorption resin column, or be dissolved in proper organic solvents and mixed with a certain volume of adsorption resin, and then loaded to an adsorption resin column. The selected solvents are capable of dispersing or dissolving lansoprazole, which may be conducted under heating. The organic solvents may be alcoholic solvents, preferably lower alcohols, such as alcohols having 1 to 4 carbon, preferably methanol, ethanol, propanol or butanol, or other organic solvents, such as ethyl acetate, dichloromethane, acetonitrile and dimethylformamide, etc. These solvents may be used alone, or in combination of two or more kinds.

The inventors found that lansoprazole compounds prepared by methods in the prior arts have high impurity contents, mainly due to the low selectivity of the oxidation step. For example N-oxide of the corresponding benzimidazole and the corresponding sulfone byproducts can be generated respectively through nitrogen oxidation and excessive oxidation of sulfide. When the methods in prior arts are scaled up, it is more difficult to control impurities. Surprisingly, by using macroporous adsorption resins, the contents of these impurities are greatly reduced.

The present invention tried a variety of substances for adsorption and purification of lansoprazole. It is surprising to find that Amberlite XAD-7, Amberlite XAD-8, DA-201, AB-8, Amberlite XAD-6, Diaion HP2MG, GDX-501, HPD400, HPD450, HPD750 and Hz841 macroporous adsorption resin columns have better separation results than alumina or silica gel column chromatography or other macroporous adsorption resin columns. They have unique purification effects and are especially suitable for industrial production.

In addition to selecting suitable resin materials, the operating environment of macroporous resin column is also related to whether the purity of lansoprazole can be effectively improved.

According to the present invention, after lansoprazole or its solution is loaded onto a macroporous adsorption resin column, first the column is rinsed with purified water and then eluted with anhydrous ethanol or mixture solvents comprising different proportions of anhydrous ethanol and other solvents, for example, the mixture solvents of anhydrous ethanol and other solvents such as ethyl acetate, dichloromethane, acetonitrile or dimethylformamide in a volume ratio of 1:1~2. The eluate is collected.

Preferably, the macroporous resin columns used in the present invention have a diameter of from about 1 to about 200 cm, preferably at least 5 cm. The length range of the macroporous resin columns preferably is about 10 cm to about 100 cm. The mass ratio of the drug to be purified to the macroporous resin is 1:10~200, preferably 1:20~100. The amount of eluent is sufficient as long as it can essentially complete the elution of the drug. The eluate fractions are collected by segments, with different segments having different drug contents. In order to obtain highly pure drug (greater than 99.5% purity), fractions with greater than 85% drug content are combined, preferably combining fractions with greater than 90% drug content. Elution rate is generally 0.1~3 BV/h, preferably 0.5~1 BV/h.

According to the present invention, then the eluate is subjected to vacuum crystallization, which comprises the steps of:

1), at least half or more of the eluate containing lansoprazole is added into a crystallization vessel and concentrated first under negative pressure and elevated temperature;

2), then the temperature is lowered and lansoprazole crystal seeds are added;

3), when fine crystal grains appear, maintaining the materials in the crystallization vessel at a boiling and concentrated state, the remaining eluate containing lansoprazole is added into the crystallization vessel, crystallization continues by keeping the temperature, and optionally the temperature may be adjusted or lowered, so that the lansoprazole solution in the crystallization vessel can further grow crystals;

4), the precipitated crystals are separated, washed and dried to provide refined lansoprazole.

The inventors found that crystallization of lansoprazole under atmospheric pressure requires very high temperature to concentrate, which has high requirements on crystallization solvents. High temperature also causes lansoprazole to melt and decompose. When crystallization is conducted under negative pressure, high temperature is not required, and it is easier to achieve the boiling and concentrated state. By controlling temperature and feeding, continuous crystallization may be carried out, which is beneficial to industrial scale production.

According to the present invention, vacuum crystallization of the lansoprazole solution is carried out in a crystallization vessel, preferably in a crystallization tank. Specific operation procedures are described below using crystallization tank as an example:

In step 1), 50-80% volume of the lansoprazole solution is added into the crystallization tank, and then the crystallization tank is vacuumed to achieve a negative pressure, such as a vacuum of −0.05 to −0.20 MPa, preferably −0.08 to −0.15 Mpa, more preferably −0.10 to −0.12 Mpa. Then by using the heating apparatus in the crystallization tank, such as by opening the hot steam valve, the system temperature reaches 70-75° C. with steam heating, to concentrate the solution by evaporation;

In step 2), evaporation is continued until the mass percentage concentration of lansoprazole in the solution reaches 40-50%, followed by cooling, for example by closing the hot steam valve, to lower the temperature naturally, for example down to 55-60° C. Then the vacuum valve is closed and the seeding valve is opened to allow rapid inhalation of the pre-prepared seed crystals of lansoprazole into the crystallization tank, followed by opening the vacuum valve to complete the seeding procedure;

In step 3), when the endoscope is covered with fine grains of crystals, the steam valve is tuned down to maintain the materials in the crystallization tank at a boiling and concentrated state, in which crystal grains grow bigger and supersaturated solutions around become less. At this point, the remaining eluate containing lansoprazole is added into the crystallization tank. Crystallization continues by controlling the temperature at 55-60° C. and continuous feeding of materials. In order to achieve more complete crystallization, through the jacket on the crystallization device, circulating water can be used to adjust or lower the temperature, not only to make the lansoprazole solution in the crystallization device further crystallize, but also to benefit the crystal growth;

In step 4), crystallization proceeds for 8-15 hours, preferably 10-12 hours, to form crystals with suitable sizes. Then the unloading valve is opened to transfer the crystalline material into a separation apparatus, such as a filter or a centrifuge. The crystals are separated via filtration or centrifugation, washed and dried to provide refined lansoprazole.

Lansoprazole crystals can be dried by solid drying agents. The solid desiccant is selected from one of these reagents: anhydrous magnesium sulfate, anhydrous calcium chloride, anhydrous calcium sulfate or activated alumina, preferably anhydrous calcium chloride.

The whole purification process in the present invention, especially the crystallization process uses less time than regular crystallization methods. Furthermore, the lansoprazole crystals obtained by the process in the present invention have grain uniformity, complete polymorph and good mobility. Comparing with the prior arts, the process disclosed in the present invention has mild conditions, low costs, high yield and high product purity, and especially it has large processing capacity, can be carried out continuously and therefore suitable for industrial production.

Given that lansoprazole's powder flowability, dissolution rate characteristics, solid stability and preparation operability all play very important roles in its activity as well as the clinical effects of formulated pharmaceutical products, lansoprazole with greatly improved purity has corresponding improvements in its dissolution rate characteristics, formulatability, and stability, improving the quality of formulated products and reducing side effects.

The present invention has fundamentally changed the current situation of low purity of the lansoprazole materials in domestic and international markets, solved the problems existing in lansoprazole crude materials and lansoprazole drug substances, reduced clinical adverse reactions, improved the quality of formulated products, and ensured the safety of clinical use of the drug. In addition, the process disclosed in the present invention has high yield and product purity of no less than 99.6%.

Embodiments of the Invention

The following examples are intended to further explain or illustrate the present invention, and the examples provided should not be understood as limiting the protective scope of the present invention.

The Purity Measurement by HPLC

Chromatographic conditions and system suitability test: octadecylsilane bonded silica as a filler; water-acetonitrile-triethylamine (60:40:1, pH value adjusted to 7.0 with phosphoric acid) as mobile phase, with detection wavelength at 285 nm. The theoretical plates calculated according to lansoprazole peak should be no less than 2000. Degree of separation between lansoprazole peak and adjacent impurity peaks should meet requirements.

Detailed procedures: Operation should be in dark places. Water-mixture solvent [acetonitrile-water-triethylamine (60:40:1) mixture solvent, pH adjusted to 7.0 using phosphoric acid] (60:40) as the mobile phase, adjusting the proportion of the mobile phase to make the retention time of the main component peak around 17 minutes. Proper amount of lansoprazole is dissolved in some amount of methanol and diluted into a solution of lansoprazole with a concentration of 1 mg/mL, as the test solution. Proper amount of lansoprazole is accurately measured and dissolved in the mobile phase to make a solution of lansoprazole with a concentration of 0.01 mg/mL, as the control solution. 10 µL of the control solution is injected into the liquid chromatograph and the detection sensitivity is adjusted to make the height of the main component chromatographic peak about 20% of the full scale of recorder; then inject 10 µL of the test solution into the liquid chromatograph, record the chromatogram to 3 times of the main component peak retention time. If there are impurity peaks in the test solution chromatogram, the area of each single impurity peak cannot be larger than half of the control solution peak area; the sum of all impurity peak areas cannot be greater than the control solution peak area.

EXAMPLE 1

100 g of brown crude lansoprazole prepared and preliminarily purified according to WO 2004/011455A1 (with a purity of 92.8% by HPLC), is dissolved in 1000 mL anhydrous ethanol under heating condition, and mixed with 100 g of pre-treated DA-201 macroporous adsorption resin. After stirring and mixing, the mixture is loaded onto the top of a DA-201 macroporous resin column. First the column is rinsed with 1~2 column volumes of purified water and then eluted with a 1:1.5 mixture solvent of anhydrous ethanol and acetonitrile. The eluate is collected.

60% volume of the obtained lansoprazole solution is added into the crystallization tank, and the crystallization tank is vacuumed to achieve a negative pressure of −0.12 MPa. Then by opening the hot steam valve on the crystallization tank, the system temperature reaches 72-75° C. with steam heating, to concentrate the solution by evaporation.

Evaporation is continued until the mass percentage concentration of lansoprazole in the solution reaches 45-50%. By closing the hot steam valve, system temperature is lowered to 55-58° C. Then the vacuum valve is closed and the seeding valve is opened to allow rapid inhalation of the pre-prepared lansoprazole seed crystals into the crystallization tank, followed by closing of the seeding valve and opening of the vacuum valve.

When the endoscope is covered with fine grains of crystals, the steam valve is tuned down to maintain the materials in the crystallization tank at a boiling and concentrated state, in which crystal grains grow bigger and supersaturated solutions around become less. At this point, the remaining eluate containing lansoprazole is added into the crystallization tank. The temperature is controlled at 55-58° C. Then through the jacket on the crystallization device, circulating water can be used to lower the temperature, to allow the lansoprazole solution to further crystallize.

Crystallization proceeds for about 10 hours to form crystals with suitable sizes. Then the unloading valve is opened to transfer the crystalline material into a filter to separate. The crystals are separated, washed with small amount of anhydrous ethanol and dried with anhydrous calcium chloride to provide 90.5 g of white lansoprazole crystals, with 99.65% purity and melting point of 170.2~170.5° C.

$^1$H-NMR δ: 11.90 (bs, 1H, NH), 8.34 (d, J=5.7 Hz, 1H, $C_5H_2N$), 7.77 (bs, 1H, $C_6H_4$), 7.46 (bs, 1H, $C_6H_4$), 7.33-7.30 (m, 2H, $C_6H_4$), 6.66 (d, J=5.7 Hz, 1H, $C_5H_2N$), 4.79 (q, $J_{H-F}$=19.0 Hz, 2H, $CH_2CF_3$), 4.37-4.32 (m, 2H, $CH_2SO$), 2.19 (s, 3H, $CH_3$);

EI-MS m/z (%): 369 ($M^+$, 13.4), 321 (50.6), 238 (100), 204 (23.1).

EXAMPLE 2

100 g of brownish lansoprazole drug substance (ZhuHai RunDu MinTong Pharmaceutical Co., Ltd., with a purity of 97.86% by HPLC), is dissolved in 1200 mL ethyl acetate under heating condition. The solution is directly loaded onto the top of a Diaion HP2MG macroporous resin column. First the column is rinsed with 1~2 column volumes of purified water and then eluted with a 1:2 mixture solvent of anhydrous ethanol and ethyl acetate. The eluate is collected.

70% volume of the obtained lansoprazole solution is added into the crystallization tank, and the crystallization tank is vacuumed to achieve a negative pressure of −0.15 MPa. Then by opening the hot steam valve on the crystallization tank, the system temperature reaches 70-73° C. with steam heating, to concentrate the solution by evaporation.

Evaporation is continued until the mass percentage concentration of lansoprazole in the solution reaches 43-45%. By closing the hot steam valve, system temperature drops naturally to 55-58° C. Then the vacuum valve is closed and the seeding valve is opened to allow rapid inhalation of the pre-prepared lansoprazole seed crystals into the crystallization tank, followed by closing of the seeding valve and opening of the vacuum valve to complete the seeding procedure.

When the endoscope is covered with fine grains of crystals, the steam valve is tuned down to maintain the materials in the crystallization tank at a boiling and concentrated state, in which crystal grains grow bigger and supersaturated solutions around become less. At this point, the remaining eluate containing lansoprazole is added into the crystallization tank. Crystallization continues by controlling the temperature at 55-58° C. and continuous feeding of materials. Then through the jacket on the crystallization device, circulating water can be used to adjust the temperature to 45-48° C. to allow the lansoprazole solution to further crystallize.

Crystallization proceeds for about 12 hours to form crystals with suitable sizes. Then the unloading valve is opened to transfer the crystalline material into a centrifuge. The crystals are separated in the centrifuge at 500 rpm and dried with anhydrous calcium chloride, to provide 90.8 g of white lansoprazole crystals, with 99.72% purity and melting point of 170.3~170.5° C.

EXAMPLE 3

100 g of expired brown lansoprazole drug substance (with a purity of 89.7% by HPLC), is mixed with 150 g of pre-treated AB-8 macroporous adsorption resin. After stirring and mixing, the mixture is loaded onto the top of an AB-8 macroporous resin column. First the column is rinsed with 1~2 column volumes of purified water and then eluted with a 1:1.2 mixture solvent of anhydrous ethanol and acetonitrile. The eluate is collected.

50% volume of the obtained lansoprazole solution is added into the crystallization tank, and the crystallization tank is vacuumed to achieve a negative pressure of −0.10 MPa. Then by opening the hot steam valve on the crystallization tank, the system temperature reaches 70-75° C. with steam heating, to concentrate the solution by evaporation.

Evaporation is continued until the mass percentage concentration of lansoprazole in the solution reaches 40-43%. By closing the hot steam valve, system temperature drops naturally to 55-60° C. Then the vacuum valve is closed and the seeding valve is opened to allow rapid inhalation of the pre-prepared lansoprazole seed crystals into the crystallization tank, followed by closing of the seeding valve and opening of the vacuum valve.

When the endoscope is covered with fine grains of crystals, the steam valve is tuned down to maintain the materials in the crystallization tank at a boiling and concentrated state, in which crystal grains grow bigger and supersaturated solutions around become less. At this point, the remaining eluate containing lansoprazole is added into the crystallization tank. The temperature is controlled at 55-60° C. Then through the jacket on the crystallization device, circulating water can be used to adjust the temperature to 45-48° C., to allow the lansoprazole solution to further crystallize.

Crystallization proceeds for about 10 hours to form crystals with suitable sizes. Then the unloading valve is opened to transfer the crystalline material into a filter. The crystals are separated by filtration, washed with small amount of water for three times and dried with anhydrous calcium chloride to provide 85.9 g of white lansoprazole crystals, with 99.58% purity and melting point of 170.2~170.4° C.

EXAMPLE 4

100 g of expired brown lansoprazole drug substance (with a purity of 90.2% by HPLC), is dissolved in 1200 mL anhydrous ethanol under heating condition, and mixed with 150 g of pre-treated Amberlite XAD-8 macroporous adsorption resin. After stirring and mixing, the mixture is loaded onto the top of an Amberlite XAD-8 macroporous resin column. First the column is rinsed with 1~2 column volumes of purified water and then eluted with a 1:1.0 mixture solvent of anhydrous ethanol and methanol. The eluate is collected.

65% volume of the obtained lansoprazole solution is added into the crystallization tank, and the crystallization tank is vacuumed to achieve a negative pressure of −0.15 MPa. Then by opening the hot steam valve on the crystallization tank, the system temperature reaches 71-74° C. with steam heating, to concentrate the solution by evaporation.

Evaporation is continued until the mass percentage concentration of lansoprazole in the solution reaches 40-45%. By closing the hot steam valve, system temperature drops naturally to 55-59° C. Then the vacuum valve is closed and the seeding valve is opened to allow rapid inhalation of the pre-prepared lansoprazole seed crystals into the crystallization tank, followed by closing of the seeding valve and opening of the vacuum valve.

When the endoscope is covered with fine grains of crystals, the steam valve is tuned down to maintain the materials in the crystallization tank at a boiling and concentrated state, in which crystal grains grow bigger and supersaturated solutions around become less. At this point, the remaining eluate containing lansoprazole is added into the crystallization tank. The temperature is controlled at 55-59° C. Then through the jacket on the crystallization device, circulating water can be used to adjust the temperature to 40-45° C., to allow the lansoprazole solution to further crystallize.

Crystallization proceeds for about 15 hours to form crystals with suitable sizes. Then the unloading valve is opened to transfer the crystalline material into a filter. The crystals are separated by filtration, washed with small amount of water for three times and dried with anhydrous calcium chloride to provide 86.9 g of white lansoprazole crystals, with 99.61% purity and melting point of 170.1~170.4° C.

EXAMPLE 5

100 g of brownish lansoprazole drug substance (ZhuHai RunDu MinTong Pharmaceutical Co., Ltd., with a purity of 97.86% by HPLC), is dissolved in 1200 mL acetonitrile under heating condition. The solution is directly loaded onto the top of a HPD750 macroporous resin column. First the column is rinsed with 1~2 column volumes of purified water and then eluted with a 1:1.4 mixture solvent of anhydrous ethanol and acetonitrile. The eluate is collected.

75% volume of the obtained lansoprazole solution is added into the crystallization tank, and the crystallization tank is vacuumed to achieve a negative pressure of −0.12 MPa. Then by opening the hot steam valve on the crystallization tank, the system temperature reaches 70-75° C. with steam heating, to concentrate the solution by evaporation.

Evaporation is continued until the mass percentage concentration of lansoprazole in the solution reaches 41-45%. By closing the hot steam valve, system temperature drops naturally to 55-60° C. Then the vacuum valve is closed and the seeding valve is opened to allow rapid inhalation of the pre-prepared lansoprazole seed crystals into the crystallization tank, followed by closing of the seeding valve and opening of the vacuum valve to complete the seeding procedure.

When the endoscope is covered with fine grains of crystals, the steam valve is tuned down to maintain the materials in the crystallization tank at a boiling and concentrated state, in which crystal grains grow bigger and supersaturated solutions around become less. At this point, the remaining eluate containing lansoprazole is added into the crystallization tank.

Crystallization continues by controlling the temperature at 55-60° C. and continuous feeding of materials.

Crystallization proceeds for about 10 hours to form crystals with suitable sizes. Then the unloading valve is opened to transfer the crystalline material into a centrifuge. The crystals are separated in the centrifuge at 500 rpm and dried with anhydrous calcium chloride, to provide 91.8 g of white lansoprazole crystals, with 99.75% purity and melting point of 170.2˜170.4° C.

The above examples fully illustrate the present invention. It should be understood that although the present invention has been illustrated according to the above examples, the foregoing description is intended to illustrate, but not to limit in any way the contents of the present invention. Numerous modifications and embodiments may be devised by the skilled in the art, without deviating the spirit and essence of the present invention. Such modifications are also understood to fall within the protective scope of the present invention. Various reference literatures cited in the present disclosure, are hereby fully cited as references.

What is claimed is:

1. A process for purifying a lansoprazole compound comprises the following steps:
   step 1) applying a crude lansoprazole material onto an adsorption resin column, which is eluted with an eluent, and collecting the eluate that containing lansoprazole;
   step 2) adding a half or more of the eluate from step 1) into a crystallization vessel, and concentrating the eluate under a negative pressure and at an elevated system temperature;
   step 3) decreasing the temperature and seeding a lansoprazole crystal;
   step 4) maintaining the mixtures at a boiling and concentrated state when fine crystal grains appear, and adding the remaining eluate from the step 1) into the crystallization vessel while stabilizing the temperature for further crystallization to obtain a precipitate; and optionally adjusting the temperature for better crystallization;
   step 5) separating, washing and drying the precipitate to yield a pure lansoprazole.

2. The process according to claim 1, in the step 1), the crude lansoprazole material is dissolved in an organic solvent and mixed with an adsorption resin, and then loaded to the adsorption resin column.

3. The process according to claim 2, the organic solvent is one or more compounds selected from the group consisting of an alcohol, an ethyl acetate, a dichloromethane, an acetonitrile and a dimethylformamide; wherein the alcohol is a lower molecule weight of alcohol selected from the group consisting of methanol, ethanol, propanol and butanol.

4. The process according to claim 1, in the step 1), the adsorption resin column is rinsed with water after the crude lansoprazole material loaded, and then eluted with an anhydrous ethanol or a mixture solvent, wherein the mixture solvent is prepared by mixing 1 part of anhydrous ethanol with 1 to 2 parts of another solvent selected from the group consisting of—ethyl acetate, dichloromethane, acetonitrile and dimethylformamide by volume.

5. The process according to claim 1, the adsorption resin column is a macroporous resin column.

6. The process according to claim 1, in the step 2), the half and more of the eluate is between 50 and 80% of the eluate; the negative pressure is −0.05 to −0.20 MPa; and a steam heating apparatus in the crystallization vessel regulates the system temperature by operating a hot steam valve, wherein the elevated system temperature is between 70 and 75° C. which concentrates the eluate by 40-50% through evaporation.

7. The process according to claim 1, in the step 3), the temperature is decreased to the range of temperature between 55 and 60° C.

8. The process according to claim 1, in step 4), the crystallization proceeds for 8-15 hours to form crystals with desired sizes.

9. The process according to claim 1, in step 5), a separation apparatus is a filter or a centrifuge used for separating the precipitate.

* * * * *